United States Patent [19]

O'Connor et al.

[11] Patent Number: 5,319,000
[45] Date of Patent: Jun. 7, 1994

[54] PROCESS FOR STABLE BIOCIDE DISPERSION

[75] Inventors: James M. O'Connor, Branford; Rahim Hani, Cheshire; Craig Waldron, Waterbury, all of Conn.

[73] Assignee: Olin Corporation, Cheshire, Conn.

[21] Appl. No.: 880,405

[22] Filed: May 8, 1992

[51] Int. Cl.$^5$ ............................................. C08K 5/12
[52] U.S. Cl. ................................................. 523/122
[58] Field of Search ...................................... 523/122

[56] References Cited

U.S. PATENT DOCUMENTS

| | | | |
|---|---|---|---|
| 3,755,224 | 8/1973 | Lutz et al. | 523/122 |
| 4,049,822 | 9/1977 | Rei et al. | 523/122 |
| 4,086,297 | 4/1978 | Rei et al. | 260/859 PV |
| 4,631,301 | 12/1986 | Kozuma et al. | 523/122 |
| 4,661,528 | 4/1987 | Rei | 523/122 |
| 4,663,359 | 5/1987 | Rei | 521/85 |
| 4,683,080 | 7/1987 | Rei et al. | 523/122 |
| 5,102,657 | 4/1992 | Rei et al. | 523/122 |

*Primary Examiner*—Paul R. Michl
*Assistant Examiner*—Edward J. Cain
*Attorney, Agent, or Firm*—Dale Lynn Carlson

[57] ABSTRACT

The present invention relates, in one aspect, to a process for preparing a storage-stable dispersion of a biocide which comprises the steps of: (a) mixing a plastisol, comprising a resin and a carrier, and a biocide to provide a mixture of said plastisol and said biocide (b) heating said mixture of plastisol and biocide to an elevated temperature of between about 30° C. and about 100° C. to provide a homogeneous, storage stable dispersion, said dispersion containing said biocide in an amount of between about one and about 30 weight percent based upon the weight of said dispersion, said resin being present in an amount of between about 5 and about 75 weight percent based upon the weight of said dispersion, with the proviso that when the weight percent of said resin in said dispersion is between about 30% and about 75%, then said elevated temperature is between 30° C. and 45° C., and when the weight percent of said resin in said dispersion is between about 5% and about 29%, then said elevated temperature is between 46° C. and 100° C., and (c) cooling the dispersion to a temperature of between about −20° C. and about 40° C. to provide a storage-stable mixture having a viscosity of between about 2,000 and about 30,000 centipoise.

14 Claims, No Drawings

PROCESS FOR STABLE BIOCIDE DISPERSION

FIELD OF THE INVENTION

The present invention relates generally to a delivery system for polymer additives, and, more specifically, to a process for providing physically stable dispersions of a biocide in a carrier/resin composition.

BACKGROUND OF THE INVENTION

Various methods for incorporating biocides into resin compositions have been disclosed in the prior art. By way of illustration, U.S. Pat. No. 4,086,297 discloses a process for forming a solid thermoplastic composition containing a microbiocide utilizing very high levels of the microbiocide and two thermoplastic resins in conjunction with melt blending processing.

As another illustration, U.S. Pat. No. 4,663,359 discloses a process for preparing a microbiocide concentrate which is useful in plastisol systems. The process comprises mixing a porous thermoplastic resin powder with a high concentration of microbiocide at an elevated temperature sufficient to melt the biocide and open the pores of the resin, and incorporating the melted biocide into the pores of the porous resin, optionally in the presence of a carrier. The resulting product is provided as a dry, free-flowing powder containing the microbiocide in a high concentration at least about 20 times greater than the normal upper usage concentration for the microbiocide.

Unfortunately, the products produced in accordance with the above-mentioned '297 and '359 patents are solids which are frequently more difficult to process into a finished product than might be desired. Liquid dispersions would avoid such solids handling problems in subsequent processing steps. Heretofore, however, suitable methods for incorporating insoluble or difficult-to-solubilize additives, such as biocides, into liquid dispersions has represented a challenge to the plastics manufacturing community. The solids in such liquid dispersions tend to settle out over time, thus causing a non-uniform distribution of the additive in the dispersion.

In view of the above, new methods for incorporating insoluble or difficult-to-solubilize biocides into plastics resins that avoid the settling and/or viscosity increase problems of the prior art compositions would be highly desired by the plastics manufacturing community.

SUMMARY OF THE INVENTION

The present invention relates, in one aspect, to a process for preparing a storage-stable dispersion of a biocide which comprises the steps of: (a) mixing a plastisol, comprising (preferably consisting essentially of) a resin and a carrier, and a biocide to provide a mixture of said plastisol and said biocide (b) heating said mixture of plastisol and biocide to an elevated temperature of between about 30° C. and about 100° C. (preferably between 30° C. and 45° C.) to provide a homogeneous, storage stable dispersion, said dispersion containing said biocide in an amount of between about one and about 30 (preferably between about 5 and about 20) weight percent based upon the weight of said dispersion, said resin being present in an amount of between about 5 and about 75 weight percent based upon the weight of said dispersion, with the proviso that when the weight percent of said resin in said dispersion is between about 30% and about 75%, then said elevated temperature is between 30° C. and 45° C., and when the weight percent of said resin in said dispersion is between about 5% and about 29%, then said elevated temperature is between 46° C. and 100° C., and (c) cooling the dispersion to a temperature of between about −20° C. and about 40° C. (preferably between 20° C. and 30° C.) to provide a storage-stable mixture having a viscosity of between about 2,000 and about 30,000 (preferably between about 5,000 and about 15,000) centipoise.

In another aspect, the present invention relates to a process for preparing a storage stable dispersion of a solid biocide which comprises the step of heating a mixture of (a) a dispersion of a solid biocide in a plasticizer and (b) a plastisol containing a carrier selected from the group consisting of phthalic acid derivatives, and epoxidized soybean oil, to an elevated temperature of between about 30° C. and about 100° C. to provide a mixture characterized by an increased viscosity sufficient to form a stable dispersion upon cooling.

These and other aspects will become apparent upon reading the following detailed description of the invention.

DETAILED DESCRIPTION OF THE INVENTION

In accordance with the present invention, it has now been surprisingly found that storage-stable dispersions of solid biocides in plastisols are provided by causing carrier absorption into the polymer to occur under elevated temperature conditions. The resulting dispersions are storage-stable against settling and against "setting-up" that would otherwise tend to occur during warehousing of the dispersions prior to use.

Plastisols useful in the process of the present invention comprise a resin plus a carrier, such as a plasticizer, including commercially available plastisols containing plasticizers and resin-compatible additives. Useful plastisols with the carriers, for example, adipic acid derivatives such as diisobutyl adipate, di-n-hexyl adipate, heptyl nonyl adipate, bis(2-ethylhexyl)adipate, diisodecyl adipate and bis(2-butoxyethyl)adipate; azelaic acid derivatives such as bis(2-ethylhexyl) azelate; benzoic acid derivatives such as diethylene glycol dibenzoate, dipropyleneglycol dibenzoate, and 2,2,4-trimethyl-1,3-pentanediol-isobutyrate benzoate; citric acid derivatives such as tri-n-butyl citrate and tri-n-butyl acetylcitrate; epoxy derivatives such as epoxidized soybean oil, epoxidized linseed oil, 2-ethylhexyl epoxy tallate and bisphenol A diglycidyl ether; glycol derivatives such as diethlyene glycol dipelargonate, triethylene glycol di-2-ethylbutyrate, and poly(ethylene glycol) (200) di-2-ethylhexanoate; glycolates such as methyl phthalyl ethyl glycolate and butylphthalyl ethyl glycolate; hydrocarbons such as hydrogenated terphenyls HB-40, poly(alkyl naphthalenes) Panaflex, aliphatic aromatics [LEROMOLL] and chlorinated paraffin (52% wt % Cl) [CERECLOR S-52]; isophthalic acid derivatives such as di-2-ethylhexyl isophthalate; oleic acid derivatives such as butyl oleate; phosphoric acid derivatives such as tributyl phosphate, tri-2-ethylhexyl phosphate, tributoxyethyl phosphate, chlorinated diphosphate [PHOSGARD 2XC-20], cresyl diphenyl phosphate, tricresyl phosphate, isopropylphenyl diphenyl phosphate [KROTINEX 100], t-butylphenyl diphenyl phosphate [SANTICIZER 154], 2-ethylhexyl diphenyl phosphate and isodecyl phosphate; phosphoric acid derivatives such as chlorinated polyphosphonate [PHOSGARD C-22-R]; phthalic acid derivatives such as dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$-$C_{11}$), ($C_6$-$C_{10}$) and ($C_8$-$C_{10}$) mixed linear phthalates [SANTICIZER 711 or PLATINOL 711P], bis(2-ethylhexyl) phthalate, diisodecyl phthalate, diundecyl phthalate, ditridecylphthalate, butyl cyclohexyl phthalate, butyl benzyl phthalate, 7-(2,6,6,8-tetramethyl-4-oxa-3-oxo-nonyl) benzyl phthalate, bis(2-butoxyethyl) phthalate, di(n-octyl) phthalate and dicylclohexyl phthalate; polyesters such as adipic acid polyester (mol wt 6000) [PARAPLEX G-40], adipic acid polyester (mol wt 2000) [SANTICIZER 334F], azelaic acid polyester (mol wt 850) [PLASTOLEIN 9720], azelaic acid polyester (mol wt 2200) [PLASTOLEIN 9750] and sebacic acid polyester; ricinoleic acid derivatives such as methyl ricinoleate, n-butyl acetylricinoleate and castor oil (90 weight percent glyceryl ricinoleate); sebacic acid derivatives such as bis(2-ethylhexyl) sebacate; stearic acid derivatives such as butyl acetoxystearate; sucrose derivatives such as sucrose acetate-isobutyrate; sulfonic acid derivatives such as N-thyl-(o,p)-toluenesulfonamide and alkylsulfonic acid ester of phenol and cresol [MESAMOLL]; terephthalic acid derivatives such as bis(2-ethylhexyl) terephthalate; and trimellitic acid derivatives such as tris(2-ethylhexyl) trimellitate, heptyl nonyl trimellitate, heptyl nonyl undecyl trimellitate and triisodecyl trimellitate.

Other useful carriers include additives not normally classified as plasticizers, such as polyols. An important criterion for the additive(s) useful as carriers within the scope of the present invention is that the additive(s) interacts with the selected swellable polymer resin upon heating to cause swelling of the polymer particles. In order for the carrier to be useful in a specific application, swelling of the polymer particles must occur at an elevated temperature below the degradation temperature of the polymer and of the carrier. Heat stabilizers can optionally be employed in order to provide elevated degradation temperatures.

The amount of carrier employed in the processes of the present invention suitably ranges between about 20 and about 95, preferably between about 50 and about 85, weight percent based upon the total weight of the dispersion.

Suitable resins in plastisol useful in the present invention include, for example, the following resins and combinations thereof: cellulosics such as cellulose acetate, cellulose acetate-butyrate, cellulose nitrate, and ethylcellulose; polyacrylates such as poly(methyl methacrylate) and acrylic copolymers, polystyrenes; polyolefins such as polyethylene and polyporopylene; polycarbonates; rubbers and synthetic elastomers; vinyl polymers such as poly(vinyl acetate), poly(vinyl butyral), poly(vinyl alcohol) and poly(vinylchloride); and polyacrylonitrile and modified copolymers thereof; and combinations thereof. The preferred resin is plastisol-grade poly(vinylchloride) ("PVC") which is typically made by emulsion polymerization and is commercially available, for example, as GEON ® 125A, a product of the BF Goodrich Company.

The amount of plastisol employed in the processes of the present invention suitably ranges between about 5 and about 75, preferably between about 25 and about 65, weight percent based upon the total weight of the dispersion.

Suitable biocides useful in the present invention include, for example, the following biocides and combinations thereof:
OBPA—10,10'-oxybisphenoxarsine
VANCIDE 89—N-(trichloromethylthio)-4-cyclohexene-1,2-dicarboximide
DOWCIL A—40-2,3,5-trichloro-4-propylsulfonyl pyridine zinc OMADINE ®-zinc salt of 1-hydroxypyridine-2-thione sodium OMADINE-sodium salt of 1-hydroxypyridine-2-thione chitosan OMADINE-chitosan pyrithione
FUNGITROL 11—N-(trichloromethylthio)phthalimide
DIFOLATAN—cis-N-(1,1,2,2-tetrachloroethyl)-thio-4-cyclohexene-1,2-dicarboximide
ISOLAN—1-isopropyl-3-methyl-5-pyrazolyl dimethyl carbamate
MANEB—manganese ethylene bisdithiocarbamate
ZINEB—zinc analog of Maneb
NABAM—disodium analog of Maneb
FERBAM—ferric dimethyl dithiocarbamate
ZIRAM—zinc analog of Ferbam
XARATHANE—2,4-dinitro-6-capryl phenol crotonate
OVATRAN—p-chlorophenyl-p-chlorobenzenesulphonate
SKANE M-8—2-N-octyl-4-isothiazolin-3-one Benomyl-methyl 1(butylcarbamoyl)-2-benzimidazole carbamate
METASOL TK-100—2(4-thiazolyl)benzimidazole Copper-8—copper 8-hydroxyquinolinate a-diethoxyphosphinodithioacetylurea a-dimethoxyphosphinodithioacetylurea Diethoxyphosphinodithioacetamide Dimethoxyphosphinodithioacetamide Bis(dimethylamido)phosphoryl fluoride Tributyl tin fluoride 2-cyclohexyl-3-isothiazolone 4,5-dichloro-2-cyclohexyl-3-isothiazolone and mixtures thereof.

The preferred biocides are sodium pyrithione, zinc pyrithione, chitosan pyrithione, and combinations thereof.

The biocide(s) is typically employed in an amount of between about one and about 30, preferably between about 5 and about 20, weight percent based upon the total weight of the dispersion. The processes of the present invention are suitable for the preparation of resin concentrates, if desired, containing high levels of biocide. The concentrates are subsequently diluted with additional polymer resin, which can be the same or different resin from that used in the preparation of the concentrate, to provide a working composition containing at least a "biocidally effective amount" of biocide, i.e., an amount of biocide sufficient to provide the desired level of biocidal efficacy in the working composition. Selection of the carrier for use in the preparation of a concentrate advantageously takes into account additives that are desirably present in the working composition. Alternatively, the working composition is suitably prepared directly using the processes of the present invention without the necessity for preparing a concentrate. The processes of the present invention are suitably effected in a few minutes or less up to ten hours or more, depending upon the specific starting materials and processing conditions employed.

Other additives are suitably optionally employed in the processes of the present invention, including for example pigments such as titanium dioxide, fillers and reinforcing agents such as glass fibers, heat stabilizers such as calcium sterate, uv stabilizers, flame retardants (e.g., phosphate and/or melamine), surfactants such as polyalkyleneoxide ethers, and the like, and combinations thereof. If used, the optional additives are suitably employed in a minor amount of less than fifty (preferably less than ten) weight percent based upon the weight of the dispersion.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

Part A—Preparation of a preliminary Zinc Pyridinethione/Plasticizer Dispersion

Butylbenzylphthalate (BBP) (2200 grams) was added to wet zinc pyridinethione filter cake (1101 grams) in a stainless steel beaker and mixed on a high speed disperser until smooth (approx. one hour). The mixture was transferred to a five liter glass round bottom flask for water removal. The mixture was stirred under vacuum as heat was slowly applied using a heating mantle. The temperature rose slowly as the water was removed. The process was halted when the temperature reached 90° C. The mixture was then allowed to cool to room temperature. This dispersion was analyzed and found to contain 21.25% zinc pyridinethione and less than 0.25% water.

Part B—Preparation of a 5% Zinc Pyridinethione Dispersion Containing 53.9% Commercial Plastisol Zinc pyridinethione dispersion (94.11 grams; 21.25% active in BBP), prepared in accordance with Part A above, was combined with 215.4 grams of commercial plastisol (containing 65% dispersion grade PVC and BBP (90.49 grams). Stirring was continued throughout the reaction. The mixture was warmed to 60° C. using an oil bath. The temperature was maintained for 5 hours. The heat was removed, and the mixture was allowed to cool. The resulting dispersion containing 5% zinc pyridinethione and 53.9% commercial plastisol was stable at room temperature and had a static viscosity of approximately 92,00 cps at 20° C.

Samples were taken at hourly intervals in order to make viscosity measurements. The dispersion viscosity was found to increase with time for each sample. The 3 samples were spun on the centrifuge for 1 hour at 2000 RMP and no separation resulted. These samples were also stored at 55° C. and were stable.

Comparative Example A

Part B—5.0% Zinc Pyridinethione in 52.6% Commercial Plastisol

Zinc pyridinethione dispersion from Example 1, Part A (26.5 grams, 20.25% active in BBP) was added to 80 grams of plastisol (containing Borden VC 440 plastisol grade PVC). The resulting formulation, prepared using typical plastisol technology, was stable at room temperature, but storage at 50° C. yielded an unacceptable solid mass.

EXAMPLE 2

Part A—Preparation of a preliminary Zinc Pyridinethione/Plasticizer Dispersion

This zinc pyridinethione concentrate was used in the below formulation. Butylbenzylphthalate (BBP) (195 grams) was added to zinc pyridinethione powder (105 grams) in a stainless steel beaker and mixed on a high speed disperser at 600 RPM for 1 hour.

Part B—Preparation of a 10% Zinc Pyridinethione Dispersion Containing 53.0% Commercial Plastisol This example was carried out utilizing a procedure similiar to the procedure of Example 1 part B, except the amounts of materials added were different. In this formulation 114.28 grams of zinc pyridinethione dispersion (35% active in BBP) was added to 212.0 grams of commercial plastisol (containing 65% dispersion grade PVC in BBP) and 73.72 grams BBP. The resulting sample was centrifuged for 1 hour at 2000 RPM resulting in no separation. The stable viscosity was 8500 cps.

EXAMPLE 3

5% Zinc Pyridinethione Dispersion in 67.9% Commercial Plastisol in Dioctyl Phthalate (DOP)

A series of stable dispersions were prepared following the procedure of Example 1 (Part A and B) by combining 67.87 grams zinc pyridinethione concentrate (22.10% active in DOP) with 203.74 grams a commercial plastisol (containing 58.9% dispersion grade PVC in DOP). 28.39 grams of DOP was also added. The sample viscosity ranged between 6,000–15,000 cps.

EXAMPLE 4

10% Zinc Pyridinethione Dispersion in 68.0% Commercial Plastisol in Dioctyl Phthalate (DOP)

Mixed 136.0 grams plastisol (containing 58.9% dispersion grade PVC in DOP), with 53.33 grams zinc pyridinethione concentrate (37.5% active in DOP) and 10.67 grams DOP. Mixed in a 1-liter flask for 1.0 hour with no heat being applied, mixing speed was approximately 400 RPM. This batch was put in an oven at 50° C. The viscosity of this sample rose for the first seven days and reached a stable viscosity of 7,200 cps after 2 weeks. This sample was centrifuged at 2000 RPM for 1 hour resulting in no separation.

EXAMPLE 5

5% Zinc Pyridinethione Dispersion in 60% Plastisol in Epoxidized Soybean Oil (ESO)

Utilized the procedure of Example 1 part A and B except for the materials. In this formulation 24.63 grams of zinc pyridinethione concentrate (40.6% active in ESO) was added to 120.0 grams of a commercial plastisol (containing 50% GEON ® 121 dispersion grade PVC) along with 55.37 grams ESO. This sample had a stable viscosity of 6300 cps.

EXAMPLE 6

10% Zinc Pyridinethione Dispersion in 56.0% Plastisol in ESO

Followed the procedure in Example 1 except the final formulation contained 10% zinc pyridinethione, 56.0% commercial plastisol and the balance was ESO. This sample had a stable viscosity of 9600 cps. This sample showed no separation after centrifuging at 2000 RPM for 1 hour.

EXAMPLE 7

5% Zinc Pyridinethione Dispersion in 50.9% Commercial Plastisol in DOP

Added 47.06 grams of zinc pyridinethione concentrate (21.25% active in DOP), 101.87 grams of commercial plastisol (containing 58.9% dispersion grade PVC in DDP), to 51.07 grams of DOP. Mixed well for 3 hours while keeping the temperature at 80° C. After 3 hours the sample was allowed to cool to room temperature. The sample reached a stable viscosity of 8080 cps after 2 days. This sample did not separate with centrifuging at 2000 RPM. The viscosity did not change by storing the sample at temperatures of less than 80° C. for an extended period of time.

What is claimed is:

1. A process for preparing a storage-stable dispersion of a biocide which comprises the steps of:
   (a) mixing a plastisol, comprising a resin and a carrier, and a biocide to provide a mixture of said plastisol and said biocide,
   (b) heating said mixture of plastisol and biocide to an elevated temperature of between about 30° C. and about 100° C. to provide a homogeneous, storage stable dispersion, said dispersion containing said biocide in an amount of between about one and about 30 weight percent based upon the weight of said dispersion, said resin being present in an amount of between about 5 and about 75 weight percent based upon the weight of said dispersion, with the proviso that when the weight percent of said resin in said dispersion is between about 30% and about 75%, then said elevated temperature is between 30° C. and 45° C., and with the further proviso that when the weight percent of said resin in said dispersion is between about 5% and about 29%, then said elevated temperature is between 46° C. and 100° C., and
   (c) cooling the dispersion to a temperature of between about $-20°$ C. and about 40° C. to provide a storage-stable mixture having a viscosity of between about 2,000 and about 30,000 centipoise.

2. The process of claim 1 wherein said biocide is selected from the group consisting of sodium pyrithione, zinc pyrithione, chitosan pyrithione, and combinations thereof.

3. The process of claim 1 wherein said biocide is employed in an amount of between about 1 and about 30 weight percent based upon the total weight of the dispersion.

4. The process of claim 1 wherein said carrier for the plastisol is selected from the group consisting of dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$–$C_{11}$), ($C_6$–$C_{10}$) and ($C_9$–$C_{10}$) mixed linear phthalates, bis(2-ethylhexyl) phthalate, diisodecyl phthalate, diundecyl phthalate, ditridecylphthalate, butyl cyclohexyl phthalate, butyl benzyl phthalate, 7-(2,6,6,8-tetramethyl-4-oxa-3-oxononyl) benzyl phthalate, bis(2-butoxyethyl) phthalate and dicylclohexyl phthalate, epoxidized soybean oil, and combinations thereof.

5. The process of claim 1 wherein said carrier is employed in an amount of between about 20 and about 95 weight percent based upon the total weight of the dispersion.

6. The process of claim 1 wherein the resin in said plastisol is polyvinyl chloride.

7. A process for preparing a storage stable dispersion of a solid biocide which comprises the step of heating a mixture of (a) a dispersion of a solid biocide in a plasticizer and (b) a plastisol containing a carrier selected from the group consisting of phthalic acid derivatives, and epoxidized soybean oil, to an elevated temperature of between about 30° C. and about 100° C. to provide a mixture characterized by an increased viscosity sufficient to form a stable dispersion upon cooling.

8. The process of claim 7 wherein said biocide is selected from the group consisting of sodium pyrithione, zinc pyrithione, chitosan pyrithione, and combinations thereof.

9. The process of claim 7 wherein said biocide is employed in an amount of between about 1 and about 30 weight percent based upon the total weight of the dispersion.

10. The process of claim 7 wherein said carrier for plastisol is selected from the group consisting of dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$–$C_{11}$), ($C_6$–$C_{10}$) and ($C_9$–$C_{10}$) mixed linear phthalates, bis(2-ethylhexyl) phthalate, diisodecyl phthalate, diundecyl phthalate, ditridecylphthalate, butyl cyclohexyl phthalate, butyl benzyl phthalate, 7-(2,6,6,8-tetramethyl-4-oxa-3-oxo-nonyl) benzyl phthalate, bis(2-butoxyethyl) phthalate and dicyclohexyl phthalate, epoxidized soybean oil, and combinations thereof.

11. The process of claim 7 wherein said carrier is employed in an amount of between about 20 and about 95 weight percent based upon the total weight of the dispersion.

12. The process of claim 7 wherein said plastisol is made of polyvinyl chloride.

13. The storage-stable composition produced by the process of claim 1.

14. The storage-stable composition produced by the process of claim 7.

* * * * *